United States Patent
Henley et al.

(10) Patent No.: US 6,885,165 B2
(45) Date of Patent: Apr. 26, 2005

(54) PATIENT BED FOR MULTIPLE POSITION EMISSION SCANS

(75) Inventors: Alan W. Henley, Knoxville, TN (US); Carlyle L. Reynolds, Powell, TN (US)

(73) Assignee: CTI PET Systems, Inc., Knoxville, TN (US)

(*) Notice: Subject to any disclaimer, the term of this patent is extended or adjusted under 35 U.S.C. 154(b) by 59 days.

(21) Appl. No.: 10/104,836

(22) Filed: Mar. 22, 2002

(65) Prior Publication Data

US 2002/0180397 A1 Dec. 5, 2002

Related U.S. Application Data

(60) Provisional application No. 60/294,713, filed on May 31, 2001.

(51) Int. Cl.[7] .............................................. G05B 11/00
(52) U.S. Cl. .......................... 318/687; 318/135; 5/611; 5/621
(58) Field of Search ...................... 5/601–611, 621–623, 5/662, 86.1; 318/687, 135, 558

(56) References Cited

U.S. PATENT DOCUMENTS

| 5,477,575 A | * | 12/1995 | Lehne et al. ................... 5/601 |
| 5,619,763 A | * | 4/1997 | Randolph et al. ............... 5/601 |
| 6,094,760 A | * | 8/2000 | Nonaka et al. ................. 5/601 |
| 6,138,302 A | * | 10/2000 | Sashin et al. .................. 5/600 |
| 6,456,684 B1 | * | 9/2002 | Mun et al. ..................... 378/20 |

* cited by examiner

Primary Examiner—Marlon Fletcher
(74) Attorney, Agent, or Firm—Pitts & Brittian, PC

(57) ABSTRACT

A patient bed for use with at least one imaging device in which a plurality of scans to be correlated are performed, as well as in a continuous motion scanner used to compile whole-body scans. The patient bed includes a horizontal rail base and a movable patient surface. Electronic controllers are provided for controlling the horizontal and vertical positioning of the patient surface. The horizontal rail base is secured to the support proximate the scanner. A linear motor is used to generate horizontal motion of the patient bed. The linear motor is controlled using a motion controller in communication with a computer associated with the imaging device. A pedestal is provided for mounting a vertical carriage assembly. A vertical track is carried by the pedestal for controlling vertical travel of the patient bed. A motor is provided for controlling vertical motion. A pallet support member is cantilevered from the vertical carriage assembly for carrying a pallet.

25 Claims, 7 Drawing Sheets

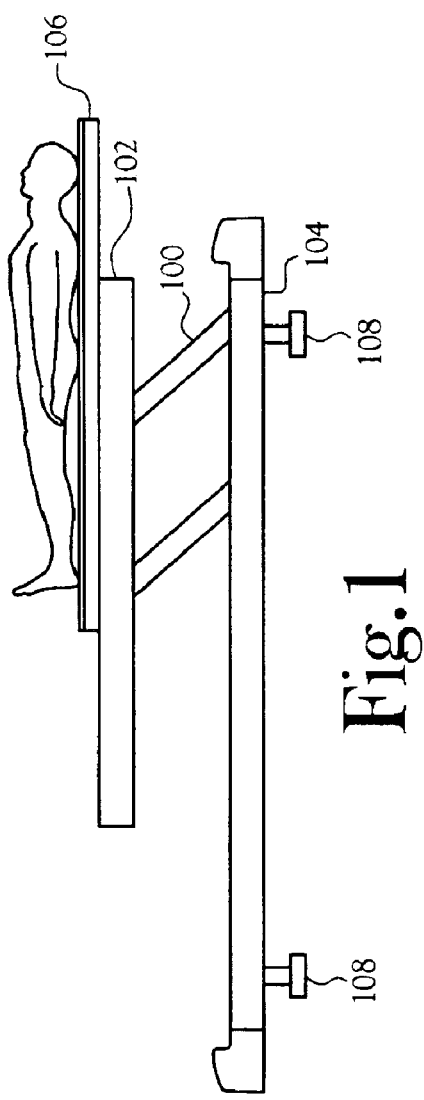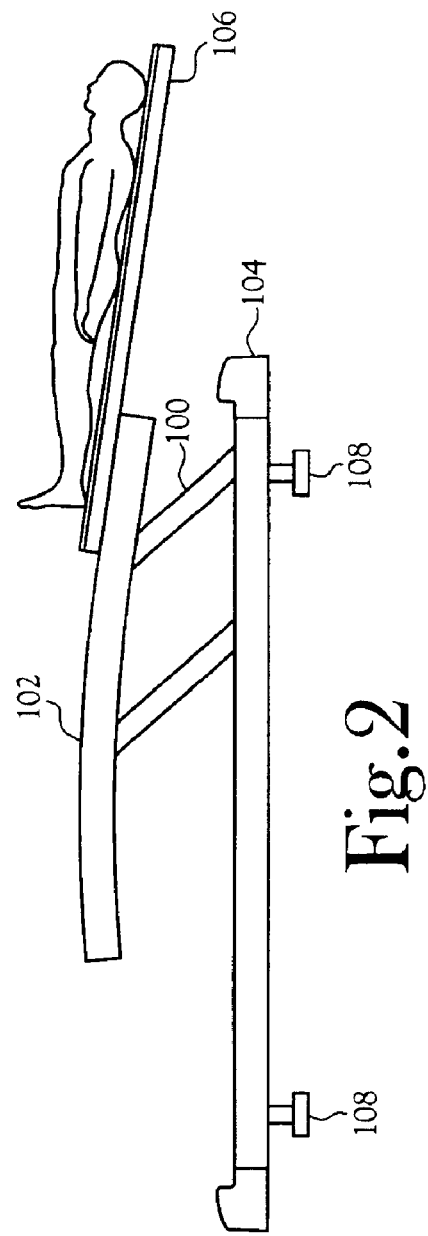

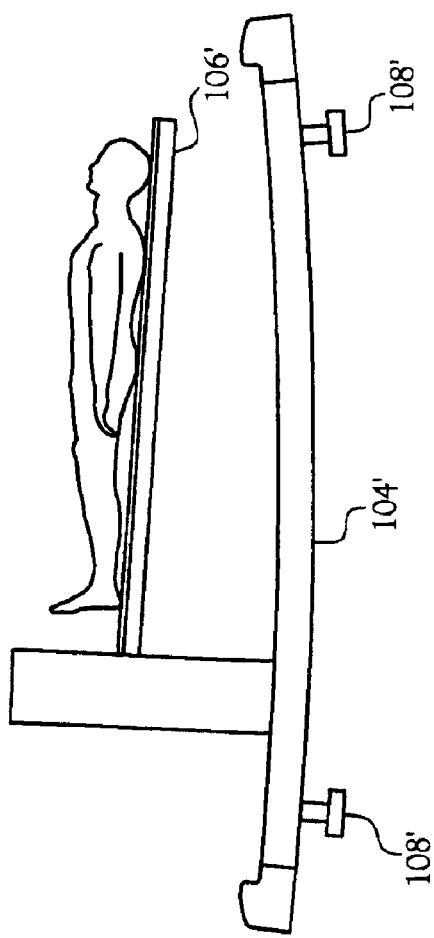
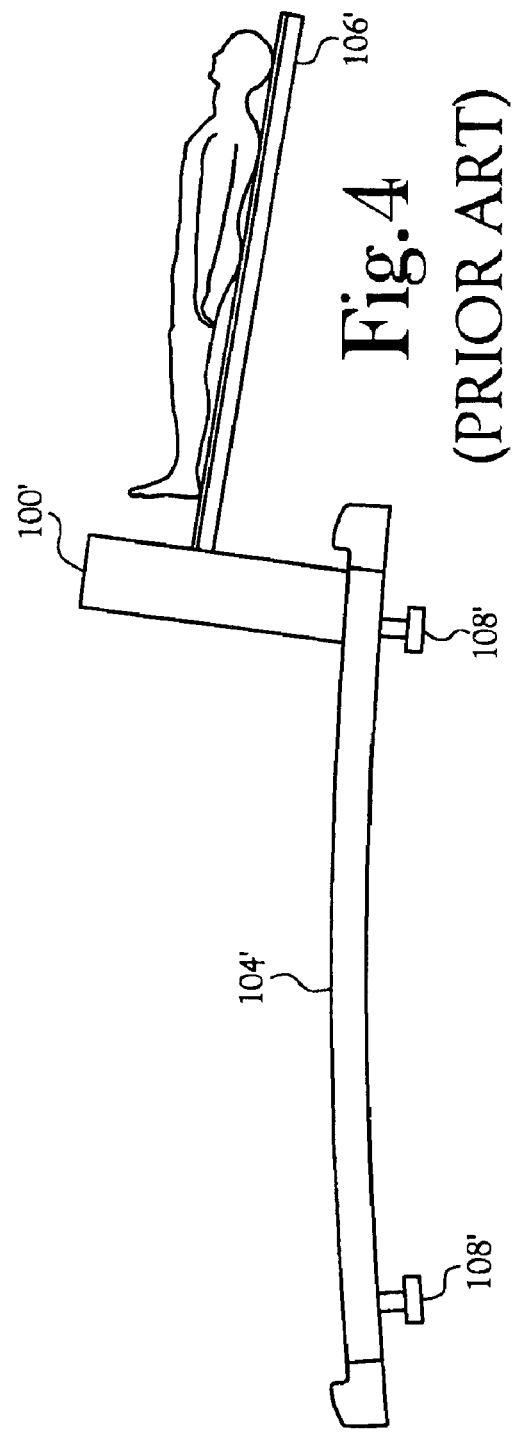

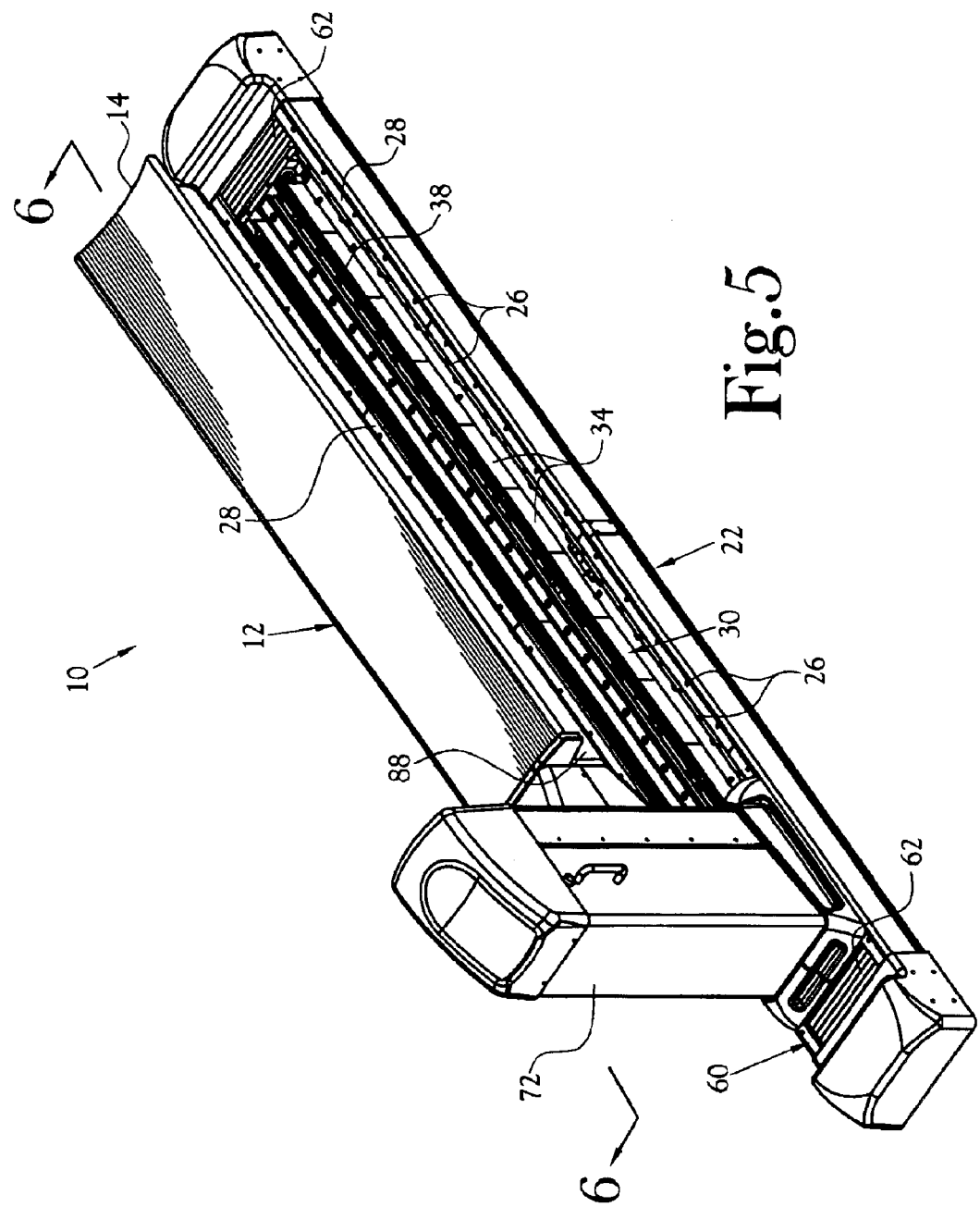

PATIENT BED FOR MULTIPLE POSITION EMISSION SCANS

CROSS-REFERENCE TO RELATED APPLICATIONS

This application claims the benefit of U.S. Provisional Application No. 60/294,713, filed May 31, 2001.

STATEMENT REGARDING FEDERALLY SPONSORED RESEARCH OR DEVELOPMENT

Not Applicable

BACKGROUND OF THE INVENTION

1. Field of Invention

This invention relates to the field of Positron Emission Tomography (PET), Computed Tomography (CT) and other related imaging devices. More specifically, the present invention is related to a patient bed for use in one or more such scanning devices which require the bed to be moved between successive scans, and in which the scans are to be used cooperatively to produce an image of the patient.

2. Description of the Related Art

In the field of medical imaging, it is well known that patients are positioned on a bed which is mechanically moved into position within a field of view of a plurality of detectors. Depending upon the type of scanner, two opposing banks of detectors or a continuous ring of detectors may be provided. A patient gantry is defined by the imaging device, the gantry being minimized in diameter in order to: minimize the cost related to the number of detectors and associated hardware; maximize the efficiency of the scan by placing the detectors as close to the patient as possible; and to minimize the overall size of the imaging device. While there are other reasons for minimizing the diameter of the patient gantry, the effect is a need for lying the patient on the bed and then inserting the bed and patient into the gantry. This is especially necessary in situations where the patient has limited mobility.

Accordingly, it is typical to lower the patient bed to a level at which the patient may comfortably be seated. The patient then reclines on the bed and is positioned for the scan. The bed is then raised to the appropriate height to be inserted into the gantry, and is then moved into the gantry. There are several common support structures for supporting the bed throughout these various positions. Illustrated in FIGS. 1 and 2 is a typical support configuration in which a rail bed 102 is disposed above a lifting mechanism 100. In the illustrated embodiment, the lifting mechanism 100 is a linkage that is pivotally mounted at each end, one to the rail bed 102 and the other to a rail base 104. A patient bed 106, or pallet, is slidably mounted on the rail bed 102. In use, the lifting mechanism 100 is lowered for loading the patient, raised to the required level for scanning, and the patient bed 106 is then extended to enter the imaging device gantry. As illustrated in FIG. 2, as the patient bed 106 is extended, the moment created by the weight of the patient and the patient bed 106 increases as it is extended, causing the distal end of the patient bed 106 to deflect downwardly. While exaggerated in the illustration, the bed deflection has been measured at up to 20 mm. Movement of the bed in both the horizontal and vertical directions is accomplished using components subject to wear, such as belt drives and screw drives.

In the illustration of FIGS. 3 and 4, another typical support configuration has the lifting mechanism disposed above the rail bed 102'. The rail bed 102' is supported on the floor by feet or casters 108'. in this embodiment, the patient bed 106' is lowered for loading the patient on the patient bed 106' and raised for extending the patient into the imaging device gantry. In this embodiment, the lifting device 100' is movable axially along the rail bed 102'. The weight of the patient, patient bed 106' and lifting mechanism 100' creates deflection of the rail bed 102' as illustrated. In FIG. 3, at particular locations of the lifting mechanism 100' along the rail bed 102', the rail bed 102' defines a concave deflection. When the lifting mechanism 100' is moved to other locations, it is seen in FIG. 4 that the rail bed 102' defines a convex configuration.

In the latter embodiment, the load of the patient bed 106' is cantilevered from the lifting mechanism 100' with no secondary support. As a result, the amplitude of vibration has been known to be excessive. As in the first prior art embodiment, movement of the bed in both the horizontal and vertical directions is accomplished using components subject to wear, such as belt drives and screw drives.

In either of these embodiments, as well as other conventional patient bed supports systems, the deflection resulting from the movement of the patient bed, whether through increased moments as a result of extending the bed, vibration of the bed as a result of movement along the rail bed, or any other change in elevation is detrimental, especially in the case of two imaging devices whose images must be correlated. Typically, as a result of a variation in elevation between scanners, vertical position correction software is required.

BRIEF SUMMARY OF THE INVENTION

The present invention is a patient bed for use with at least one imaging device, or scanner, in which a plurality of scans are performed, each of the scans being correlated to the other scans. The present invention is useful in a continuous motion scanner used to compile whole-body scans, as well as dual scanners such as a combined Positron Emission Tomography-Computed Tomography (PET-CT) scanner.

The patient bed includes primarily a horizontal rail base and a movable patient surface. An electronic controller controls the horizontal and vertical positioning of the patient surface. The horizontal rail base is secured to the support proximate the scanner. A leveling compound, such as an epoxy, is poured into a form approximately the size of the rail base. The rail base is secured to the leveling compound with a series of anchor bolts. A side rail is mounted along each side of the rail base. The side rails are provided for supporting the patient bed as it is moved along the base.

Centrally disposed between the side rails is a magnetic track used in cooperation with a linear motor. Segments of the magnetic track are secured to the base using bolts. A channel is defined by the magnetic track in which is received a linear motor. The horizontal motion of the patient bed is controlled using a motion controller in communication with a gantry move interface of a computer associated with the imaging device. A position encoder is used for horizontal positioning.

Horizontal travel is limited at either end by a mechanical stop. A limit switch is disposed on an inboard side of each mechanical stop. An optical sensor is disposed at a predetermined position between the limit switch and the mechanical stop. The sensor serves as a home/zero position sensor.

A horizontal bearing plate is mounted on the top of the linear motor. A pedestal plate is mounted on the top of the horizontal bearing plate, the pedestal plate being provided for carrying a pedestal. In order to protect the magnetic track and linear motor, a cover assembly is supplied on either end of the pedestal plate.

The pedestal is provided for mounting a vertical carriage assembly. A vertical track is carried by the pedestal for controlling vertical travel of the patient bed. A housing assembly is provided for covering the pedestal and other components utilized for raising and lowering the patient bed. A motor is mounted within the housing assembly for controlling vertical motion. The motor incorporates a positioning encoder for monitoring the current vertical position of the patient bed. An end stop system is also incorporated in the motor for cutting power from the motor at the end of a stroke. A mechanical stop is also provided for limiting upward vertical motion.

In order to ensure that the pallet is positioned within the gantry opening before allowing horizontal movement, a scan position switch is provided. At a predetermined location between the scan position switch and the mechanical stop is disposed an optical sensor. The optical sensor is provided as a home/zero position sensor.

A pallet support member is cantilevered from the vertical carriage assembly, the pallet support being provided for carrying a pallet. A base plate is mounted on the vertical bearing plate and is provided for mounting the support beam. A saddle is carried by the distal end of the support beam for receiving the pallet at an approximate midpoint. At least one gusset is provided on each of the upper and lower surfaces of the support beam and is secured to the base plate for stabilizing the support beam to minimize deflection of the support beam, and ultimately the pallet, when a load is placed thereon.

The patient bed is configured such that a patient lying thereon, as well as parts of the bed, including accessories, do not come into contact with the gantry during horizontal and vertical movement of the bed.

BRIEF DESCRIPTION OF THE SEVERAL VIEWS OF THE DRAWINGS

The above-mentioned features of the invention will become more clearly understood from the following detailed description of the invention read together with the drawings in which:

FIG. 1 is a schematic illustration of a prior art device wherein the rail bed is disposed above a lifting mechanism, a patient bed being slidably mounted on the rail bed, wherein the patient bed is illustrated in the retracted position;

FIG. 2 is a schematic illustration of the prior art device of FIG. 1 wherein the patient bed is illustrated in the extended position;

FIG. 3 is a schematic illustration of a prior art device wherein the lifting mechanism disposed above the rail bed, wherein moments created by a load on the patient bed create a concave deformation of the rail bed;

FIG. 4 is a schematic illustration of the prior art device of FIG. 3 wherein moments created by a load on the patient bed create a convex deformation of the rail bed;

FIG. 5 is a perspective illustration of the patient bed of the present invention;

DETAILED DESCRIPTION OF THE INVENTION

A patient bed for multiple position emission scans incorporating various features of the present invention is illustrated generally at 10 in the figures. The patient bed 10 is provided for use with at least one imaging device 18, or scanner, in which a plurality of scans are performed, each of the scans being correlated to the other scans. The present invention is useful in a continuous motion scanner used to compile whole-body scans, as well as dual scanners such as a combined Positron Emission Tomography-Computed Tomography (PET-CT) scanner. Although the present invention is described herein with use in conjunction with a combined PET-CT scanner, it will be understood that the patient bed 10 of the present invention is useful in other emission scanners as well.

The patient bed 10 is controlled to position the patient for the taking of CT and PET fused images. The patient bed 10 is designed to maintain constant vertical positioning of the patient through two scanner fields of view, irrespective of horizontal position. As illustrated in FIG. 5, the patient bed 10 includes primarily a horizontal rail base 22 and a movable patient surface 12. Electronic controllers are provided for controlling the horizontal and vertical positioning of the patient surface 12.

Figure 6:
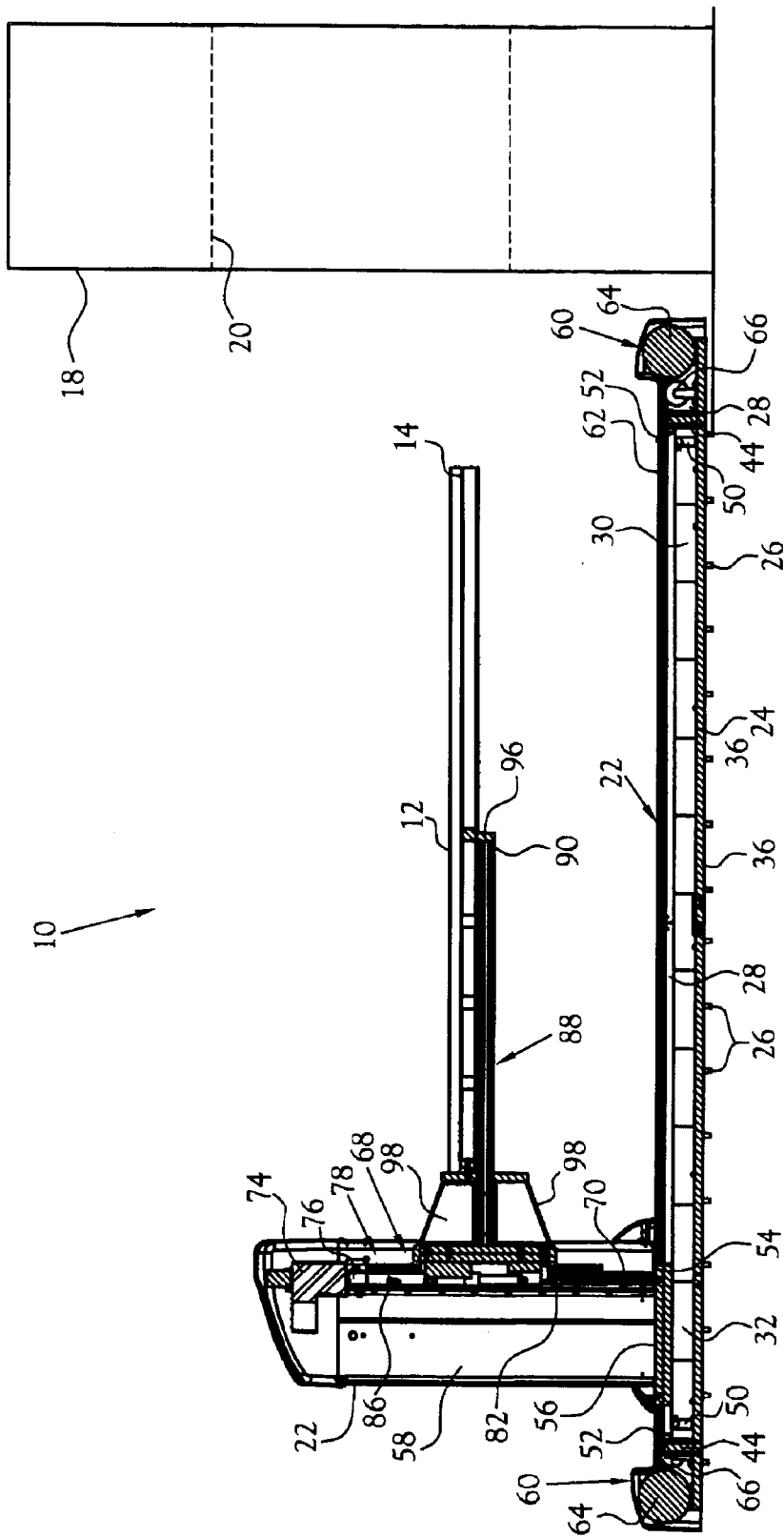
FIG. 6 is a side elevation view of the present invention, in section taken at 6—6 of FIG. 5.

As best illustrated in FIG. 6, the horizontal rail base 22 is secured to the support proximate the scanner 18. A leveling compound 24, such as an epoxy, is poured into a form approximately the size of the rail base 22. The rail base 22 is secured to the leveling compound 24 with a series of securement devices 26 such as the illustrated anchor bolts. A side rail 28 is mounted along each side of the rail base 22. The side rails 28 are provided for supporting the patient bed 12 as it is moved along the base 22.

Centrally disposed between the side rails 28 is a magnetic track 30 used in cooperation with a linear motor 32 such as the LM310 brushless linear motor manufactured by Trilogy Systems, Webster, Tex. Segments 34 of the magnetic track 30 are secured to the base 22 in a conventional manner such as by the illustrated bolts 36. A channel 38 is defined by the magnetic track 30 in which is received the linear motor 32.

Figure 7:
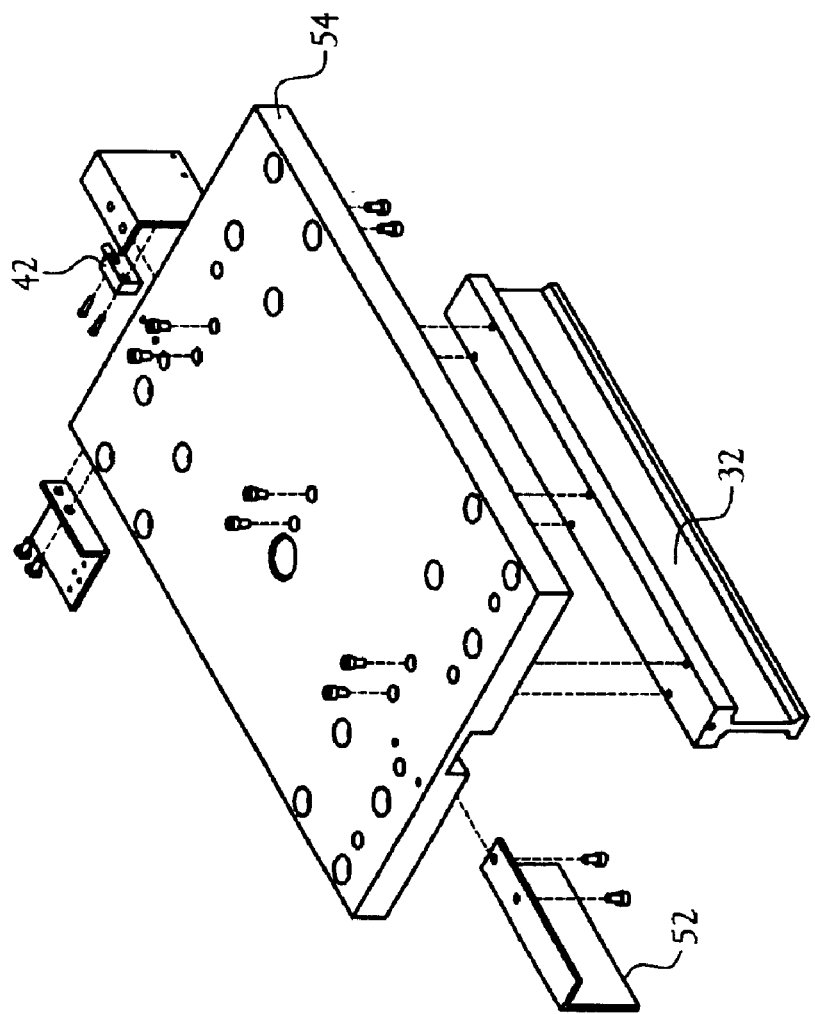
FIG. 7 is an exploded view of the horizontal linear motor and horizontal base plate incorporated in the present invention.

Referring to FIG. 7, the horizontal motion of the patient bed 12 is controlled using a motion controller 40 such as the Hauser COMPAX 2500s motion controller. The motion controller 40 is in communication with a gantry move interface of a computer (not shown) associated with the imaging device 18. A position encoder 42 such as a sin/cos magnetic incremental encoder is used for horizontal positioning. The encoder 42 of the preferred embodiment has a signal period of at most 1 mm. A signal from the encoder 42 is delivered to the motion controller 40 and translated to quadrature pulses for the imaging device gantry 20. In an alternate embodiment, not shown, an absolute system is incorporated to allow the position of the patient bed 12 to always be known, thus eliminating the need for a homing procedure on power up.

Horizontal travel is limited at either end by a mechanical stop 44. A limit switch 50 is disposed on an inboard side of each mechanical stop 44. Once the linear motor 32 reaches the limit switch 50, the limit switch 50 is opened. The limit switch 50 remains open until the mechanical stop 44 is reached. A sensor 52 such as an optical sensor is disposed at a predetermined position between the limit switch 50 and the mechanical stop 44. The sensor 52 serves as a home/zero position sensor. The optical sensor 52 of the illustrated embodiment is blocked upon arrival of the linear motor 32, and remains blocked as the linear motor 32 arrives at the mechanical stop 44. Because the distances away from the mechanical stop 44 of each of the limit switch 50 and the optical sensor 52 are known, the linear motor 32 is controlled to stop upon or prior to reaching the mechanical stop 44.

Figure 8:
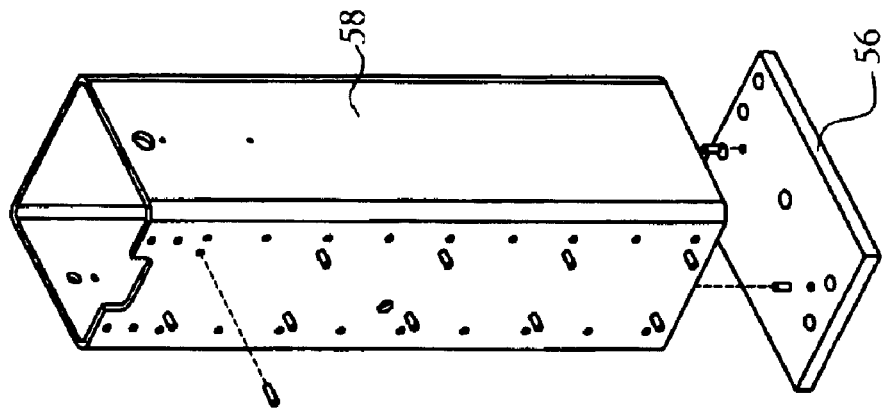
FIG. 8 is an exploded view of the pedestal plate and pedestal incorporated in the present invention.

A horizontal bearing plate 54 is mounted on the top of the linear motor 32. A pedestal plate 56 is mounted on the top of the horizontal bearing plate 54, the pedestal plate 56 being provided for carrying a pedestal 58, as illustrated in FIG. 8. In order to protect the magnetic track 30 and linear motor 32, a cover assembly 60 (FIGS. 5 and 6) is supplied on either end of the pedestal plate 56. Each cover assembly 60 includes a cover member 62 dimensioned to extend substantially along the length of the base 22 and to extend at least between the side rails 28. The cover member 62 is fabricated from a material capable of being received on a spool 64. The spool 64 is disposed at the end of the base 22. In order to maintain a consistent height of the cover member 62, a pair of casters 66 is disposed proximate the spool 64 between the spool 64 and the pedestal plate 56. The cover member 62 rests on the top of the casters 66. As the linear motor 32 is actuated in either direction, the horizontal bearing plate 54 and the pedestal plate 56 are moved along the length of the base 22. Consequently, the cover member 62 of one cover assembly 60 is retracted onto the respective spool 64 while the cover member 62 of the other cover assembly 60 is extended from its spool 64.

Figure 9:
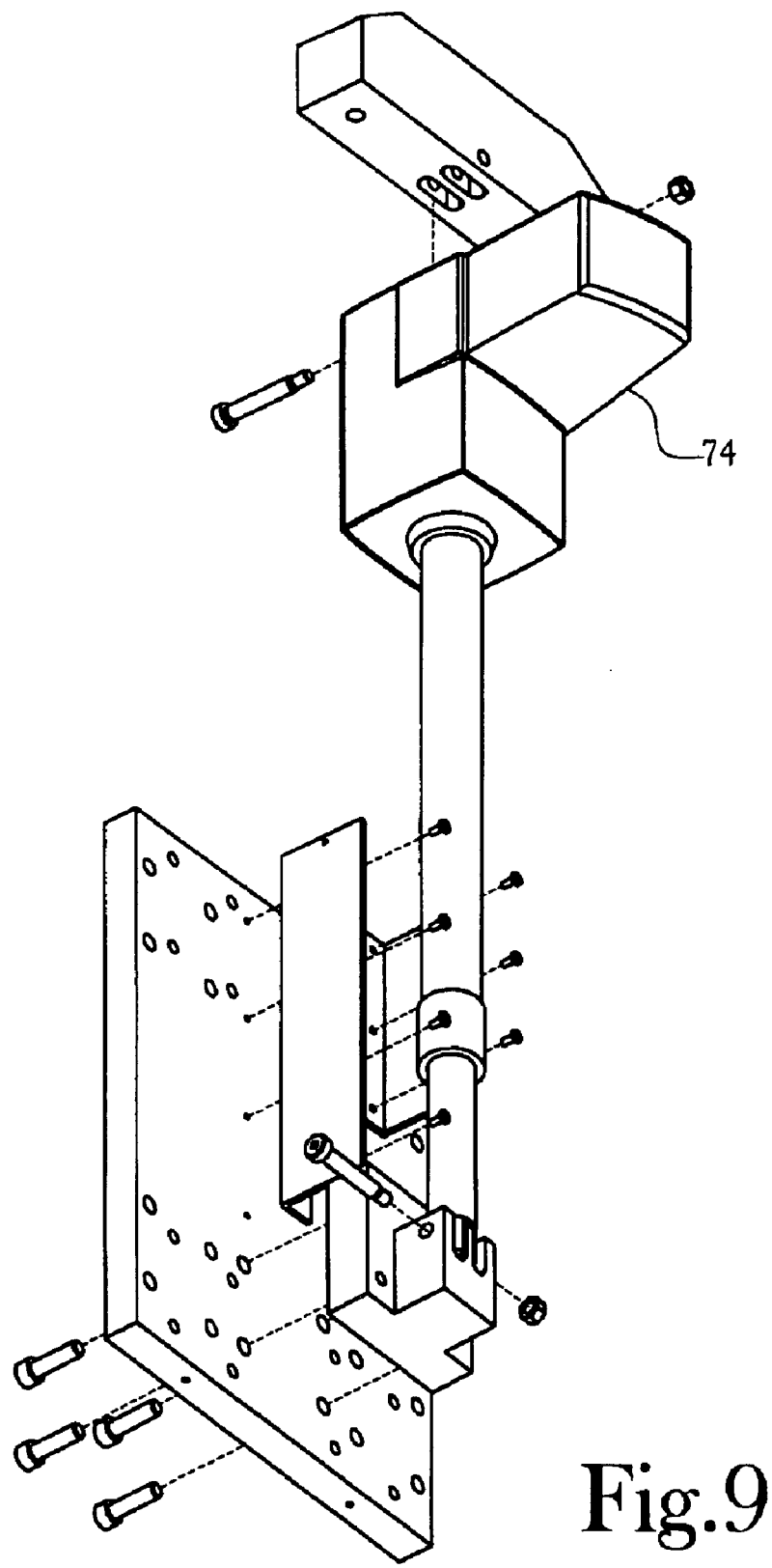
FIG. 9 is an exploded view of the vertical bearing plate and vertical linear actuator incorporated in the present invention.

The pedestal 58 is provided for mounting a vertical carriage assembly 68. A vertical track 70 is carried by the pedestal 58 for controlling vertical travel of the patient bed 12. A housing assembly 72 (FIG. 6) is provided for covering the pedestal 58 and other components utilized for raising and lowering the patient bed 12. A motor 74, illustrated best in FIG. 9, is mounted within the housing assembly 72 for controlling vertical motion. In the preferred embodiment, the motor 74 is a DC brush type motor such as the LA34 linear actuator manufactured by Linak U.S., Inc., Louisville, Ky. In such a motor 74, a positioning encoder 76 is provided to monitor the current vertical position of the patient bed 12. An end stop system 78 is also incorporated in the motor 74 for cutting power from the motor 74 at the end of a stroke. A mechanical stop 80 is also provided for limiting upward vertical motion.

Vertical positioning is accomplished using a quadrature pulse encoder 82. In the preferred embodiment, the quadrature pulse encoder 82 has a minimum resolution of 10 pulses per mm. The position read from the controller is a factor of 10 greater than the actual pallet 12 position. The actual pallet 12 position is found, while the bed 12 is unloaded, by measuring from the uppermost edge, at the lowest point 14 of the curve in the pallet 12, to the bottom of the floor plate. Detection of the vertical position is available through the entire length of travel.

In order to ensure that the pallet 12 is positioned within the gantry 20 opening before allowing horizontal movement, a scan position switch 84 is provided. The scan position switch 84 is positioned at a predetermined distance below the mechanical stop 80. After the actuator 74 reaches the scan position switch 84, the scan position switch 84 opens and remains open up to the mechanical limit of the actuator 74.

At a predetermined location between the scan position switch 84 and the mechanical stop 80 is disposed an optical sensor 86. The optical sensor 86 is provided as a home/zero position sensor. The optical sensor 86 is preferably disposed proximate the scan position switch 84 to maximize the probability of pass through with each scan.

Figure 10:
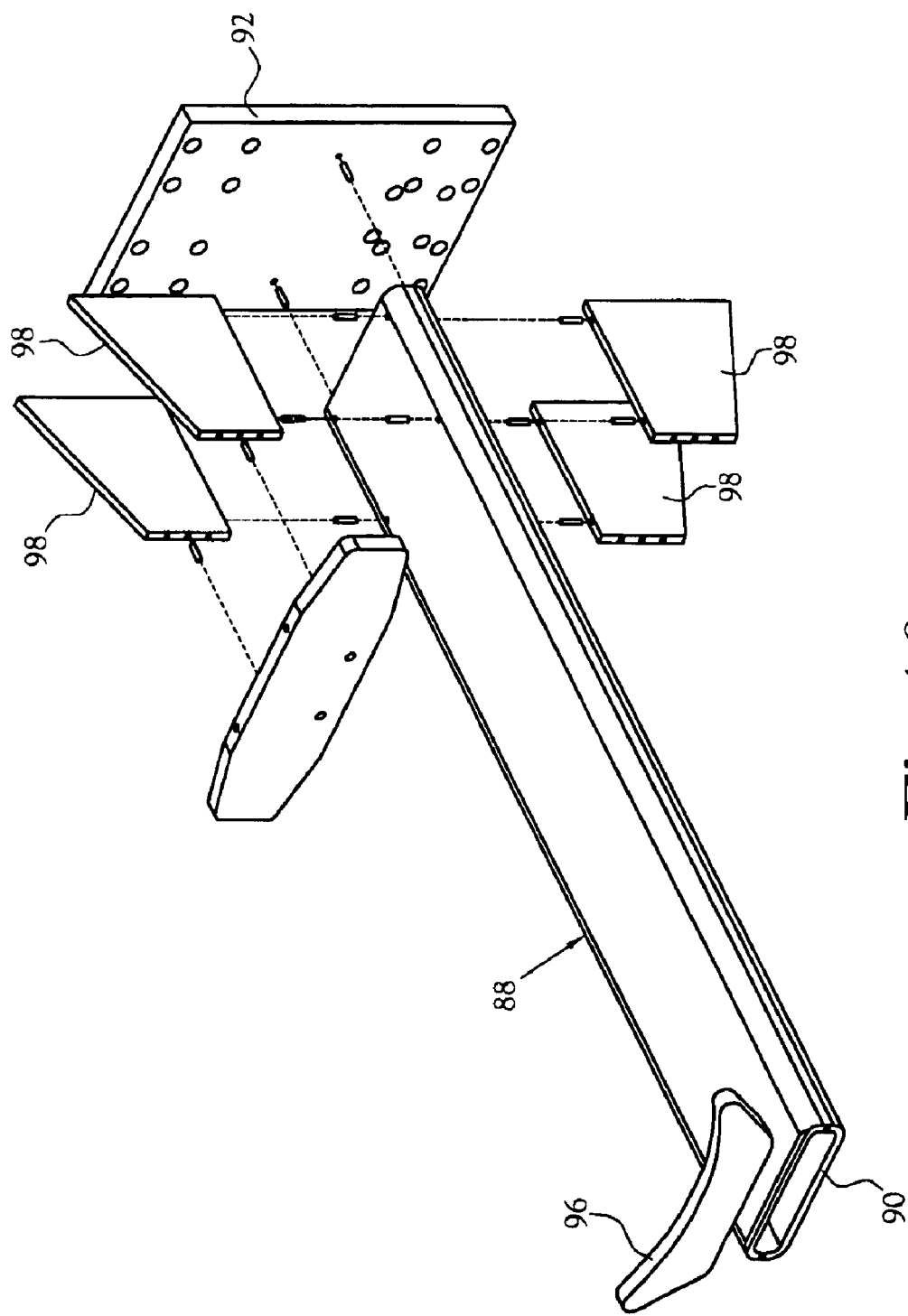
FIG. 10 is an exploded view of the pallet support incorporated in the present invention.

A pallet support member 88, illustrated in FIG. 10, is cantilevered from the vertical carriage assembly 68, the pallet support 88 being provided for carrying the pallet 12. A base plate 92 is mounted on a vertical bearing plate 94 and is provided for mounting the support beam 88. The support beam 88 extends approximately one half the length of the pallet 12. A saddle 96 is carried by the distal end 90 of the support beam 88 for receiving the pallet 12 at an approximate midpoint. At least one gusset 98 is provided on each of the upper and lower surfaces of the support beam 88 and is secured to the base plate 92. Illustrated are two gussets 98 disposed on each of the upper and lower surfaces of the support beam 88. The gussets 98 serve to stabilize the support beam 88 to minimize deflection of the support beam 88, and ultimately the pallet 12, when a load is placed thereon.

The patient bed 10 is configured such that a patient lying thereon, as well as parts of the bed 10, including accessories, do not come into contact with the gantry 20 during horizontal and vertical movement of the bed 10. The pallet 12, including any attachments, is free from foreign body inclusions over the whole irradiable area and allows radiation to pass through artifact-free.

From the foregoing description, it will be recognized by those skilled in the art that a patient bed for multiple position emission scans offering advantages over the prior art has been provided. Namely, the patient bed of the present invention provides a device for use with at least one imaging device, or scanner, in which a plurality of scans are performed, each of the scans being correlated to the other scans. The present invention is also useful in a continuous motion scanner used to compile whole-body scans, as well as dual scanners such as a combined Positron Emission Tomography-Computed Tomography (PET-CT) scanner. The patient bed is designed to maintain constant vertical positioning of the patient through two scanner fields of view, irrespective of horizontal position.

While the present invention has been illustrated by description of several embodiments and while the illustrative embodiments have been described in considerable detail, it is no the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A patient bed adapted to be received within a gantry of at least one imaging device for a multiple position emission scan, said patient bed comprising:
   a horizontal rail base secured to a support surface;
   a magnetic track disposed along a length of said horizontal rail base;
   a linear motor cooperating with said magnetic track to impart horizontal motion on said linear motor along said length of said horizontal rail base, said linear motor being actuated to move said linear motor along said magnetic track;

a pedestal carried by said linear motor, whereby as said linear motor is moved along said magnetic track, said pedestal is moved horizontally along said length of said rail base;

a vertical track carried by said pedestal for controlling vertical travel of said patient bed;

a linear actuator for imparting vertical motion along said vertical track;

a pallet support member carried by said linear actuator, said pallet support member defining a substantially planar member having a proximal and a distal end, said proximal end being secured to said linear actuator and said distal end being cantilevered from said linear actuator; and a pallet for holding a patient during the emission scan, said pallet being disposed above said pallet support member and defining a proximal end and a distal end, said proximal end being secured proximate said pallet support member proximal end, said pallet support member distal end engaging said pallet along a length thereof whereby said pallet is maintained at a constant vertical position irrespective of horizontal position.

2. The patient bed of claim 1 further comprising a horizontal motion controller in communication with a computer associated with the imaging device for controlling said linear motor.

3. The patient bed of claim 1 further comprising a vertical motion controller in communication with a computer associated with the imaging device for controlling said linear actuator.

4. The patient bed of claim 1 further comprising a position switch to ensure that said pallet is disposed at a height to allow entry into the imaging device gantry before allowing said horizontal motion.

5. The patient bed of claim 1 further comprising a position switch to ensure that said pallet is disposed at a height to allow entry into the imaging device gantry before allowing said horizontal motion.

6. A patient bed adapted to be received within a gantry of at least one imaging device for a multiple position emission scan, said patient bed comprising:

a horizontal rail base secured to a support surface;

a magnetic track disposed along a length of said horizontal rail base;

a linear motor cooperating with said magnetic track to impart horizontal motion along said length of said horizontal rail base;

a horizontal position encoder for monitoring a horizontal position of said linear motor with respect to said horizontal rail base;

a pedestal carried by said linear motor;

a vertical track carried by said pedestal for controlling vertical travel of said patient bed;

a linear actuator for imparting vertical motion along said vertical track;

a vertical position encoder for monitoring a vertical position of said linear actuator with respect to said vertical track;

a pallet support member carried by said linear actuator, said pallet support member defining a substantially planar member having a proximal and a distal end, said proximal end being secured to said linear actuator and said distal end being cantilevered from said linear actuator; and a pallet for holding a patient during the emission scan, said pallet being disposed above said pallet support member and defining a proximal end and a distal end, said proximal end being secured proximate said pallet support member proximal end, said pallet support member distal end engaging said pallet along a length thereof whereby said pallet is maintained at a constant vertical position irrespective of horizontal position.

7. The patient bed of claim 6 further comprising a leveling compound disposed on said support surface, said horizontal rail base being disposed on said leveling compound in order to minimize deflection of said pallet during horizontal motion thereof.

8. The patient bed of claim 6 further comprising a horizontal motion controller in communication with a computer associated with the imaging device for controlling said linear motor.

9. The patient bed of claim 6 further comprising a vertical motion controller in communication with a computer associated with the imaging device for controlling said linear actuator.

10. The patient bed of claim 6 further comprising a position switch to ensure that said pallet is disposed at a height to allow entry into the imaging device gantry before allowing said horizontal motion.

11. A patient bed adapted to be received within a gantry of at least one imaging device for a multiple position emission scan, said patient bed comprising:

a horizontal rail base secured to a support surface;

a magnetic track disposed along a length of said horizontal rail base;

a linear motor cooperating with said magnetic track to impart horizontal motion along said length of said horizontal rail base;

a pedestal carried by said linear motor;

a vertical track carried by said pedestal for controlling vertical travel of said patient bed;

a linear actuator for imparting vertical motion along said vertical track;

a pallet support member carried by said linear actuator, said pallet support member defining a substantially planar member having a proximal and a distal end, said proximal end being secured to said linear actuator and said distal end being cantilevered from said linear actuator;

a pallet for holding a patient during the emission scan, said pallet being disposed above said pallet support member and defining a proximal end and a distal end, said proximal end being secured proximate said pallet support member proximal end, said pallet support member distal end engaging said pallet along a length thereof whereby said pallet is maintained at a constant vertical position irrespective of horizontal position; and a leveling compound disposed on said support surface, said horizontal rail base being disposed on said leveling compound in order to minimize deflection of said pallet during horizontal motion thereof.

12. The patient bed of claim 11 further comprising a horizontal motion controller in communication with a computer associated with the imaging device for controlling said linear motor.

13. The patient bed of claim 11 further comprising a vertical motion controller in communication with a computer associated with the imaging device for controlling said linear actuator.

14. The patient bed of claim 11 further comprising a horizontal position encoder for monitoring a horizontal position of said linear motor with respect to said horizontal rail base.

15. The patient bed of claim 11 further comprising a vertical position encoder for monitoring a vertical position of said linear actuator with respect to said vertical track.

16. The patient bed of claim 11 further comprising a position switch to ensure that said pallet is disposed at a height to allow entry into the imaging device gantry before allowing said horizontal motion.

17. A patient bed adapted to be received within a gantry of at least one imaging device for a multiple position emission scan, said patient bed comprising:

a horizontal rail base secured to a support surface;

a magnetic track disposed along a length of said horizontal rail base;

a linear motor cooperating with said magnetic track to impart horizontal motion along said length of said horizontal rail base;

a horizontal position encoder for monitoring a horizontal position of said linear motor with respect to said horizontal rail base;

a pedestal carried by said linear motor;

a vertical track carried by said pedestal for controlling vertical travel of said patient bed;

a linear actuator for imparting vertical motion along said vertical track;

a pallet support member carried by said linear actuator, said pallet support member defining a substantially planar member having a proximal and a distal end, said proximal end being secured to said linear actuator and said distal end being cantilevered from said linear actuator; and a pallet for holding a patient during the emission scan, said pallet being disposed above said pallet support member and defining a proximal end and a distal end, said proximal end being secured proximate said pallet support member proximal end, said pallet support member distal end engaging said pallet along a length thereof whereby said pallet is maintained at a constant vertical position irrespective of horizontal position.

18. The patient bed of claim 17 further comprising a leveling compound disposed on said support surface, said horizontal rail base being disposed on said leveling compound in order to minimize deflection of said pallet during horizontal motion thereof.

19. The patient bed of claim 17 further comprising a horizontal motion controller in communication with a computer associated with the imaging device for controlling said linear motor.

20. The patient bed of claim 17 further comprising a vertical motion controller in communication with a computer associated with the imaging device for controlling said linear actuator.

21. A patient bed adapted to be received within a gantry of at least one imaging device for a multiple position emission scan, said patient bed comprising:

a horizontal rail base secured to a support surface;

a magnetic track disposed along a length of said horizontal rail base;

a linear motor cooperating with said magnetic track to impart horizontal motion along said length of said horizontal rail base;

a pedestal carried by said linear motor;

a vertical track carried by said pedestal for controlling vertical travel of said patient bed;

a linear actuator for imparting vertical motion along said vertical track;

a vertical position encoder for monitoring a vertical position of said linear actuator with respect to said vertical track;

a pallet support member carried by said linear actuator, said pallet support member defining a substantially planar member having a proximal and a distal end, said proximal end being secured to said linear actuator and said distal end being cantilevered from said linear actuator; and a pallet for holding a patient during the emission scan, said pallet being disposed above said pallet support member and defining a proximal end and a distal end, said proximal end being secured proximate said pallet support member proximal end, said pallet support member distal end engaging said pallet along a length thereof whereby said pallet is maintained at a constant vertical position irrespective of horizontal position.

22. The patient bed of claim 21 further comprising a leveling compound disposed on said support surface, said horizontal rail base being disposed on said leveling compound in order to minimize deflection of said pallet during horizontal motion thereof.

23. The patient bed of claim 21 further comprising a horizontal motion controller in communication with a computer associated with the imaging device for controlling said linear motor.

24. The patient bed of claim 21 further comprising a vertical motion controller in communication with a computer associated with the imaging device for controlling said linear actuator.

25. The patient bed of claim 21 further comprising a position switch to ensure that said pallet is disposed at a height to allow entry into the imaging device gantry before allowing said horizontal motion.

* * * * *